United States Patent
Brown

(10) Patent No.: US 6,745,501 B2
(45) Date of Patent: Jun. 8, 2004

(54) ORTHOTIC FOR IMPROVING TOE-OFF ACTION OF HUMAN FOOT

(75) Inventor: Dennis N Brown, Blaine, WA (US)

(73) Assignee: Northwest Podiatric Laboratory, Inc., Blaine, WA (US)

( * ) Notice: Subject to any disclaimer, the term of this patent is extended or adjusted under 35 U.S.C. 154(b) by 0 days.

(21) Appl. No.: 09/810,826

(22) Filed: Mar. 16, 2001

(65) Prior Publication Data

US 2002/0133109 A1 Sep. 19, 2002

(51) Int. Cl.$^7$ ............................. A61F 5/14; A43B 7/18
(52) U.S. Cl. ........................................ 36/174; 36/180
(58) Field of Search ............... 602/66–73, 28–30; 36/43–44, 71, 167–168, 174–176, 177–180, 76 C, 108

(56) References Cited

U.S. PATENT DOCUMENTS

| | | | | |
|---|---|---|---|---|
| 4,573,457 A | * | 3/1986 | Parks | 602/29 |
| 4,686,993 A | * | 8/1987 | Grumbine | 36/140 |
| 4,747,410 A | * | 5/1988 | Cohen | 36/140 |
| 4,800,657 A | * | 1/1989 | Brown | 36/115 |
| 5,240,773 A | * | 8/1993 | Dunn | 428/408 |
| 5,394,626 A | * | 3/1995 | Brown | 36/173 |
| 5,647,147 A | * | 7/1997 | Coomer | 36/93 |
| 5,722,186 A | * | 3/1998 | Brown | 36/140 |
| 5,946,825 A | * | 9/1999 | Koh et al. | 36/44 |
| 6,125,557 A | * | 10/2000 | Brown | 36/144 |

* cited by examiner

Primary Examiner—Danton D. DeMille
Assistant Examiner—Quang D Thanh
(74) Attorney, Agent, or Firm—Todd N. Hathaway

(57) ABSTRACT

A removable orthotic insert for improving the gait of a person suffering from diabetes, rheumatoid arthritis, or other condition that impairs proper transfer of weight to the forefoot. There is a rigid cap member having a downwardly extending, transverse ridge located proximate the junction between the arch and forefoot portions of the insert, behind the metatarsal head area of the foot. The ridge engages the underlying insole of the shoe to form a pivot point that enables the insert to rock forwardly and rearwardly in the shoe. As the person's foot moves through the gait cycle, the transfer of weight towards the forward end of the foot causes the rigid cap member to tilt forwardly in the shoe, enhancing the angular orientation of the foot as the toe-off position is reached.

21 Claims, 5 Drawing Sheets

ABNORMAL GAIT CYCLE

ORTHOTIC FOR IMPROVING TOE-OFF ACTION OF HUMAN FOOT

BACKGROUND OF THE INVENTION a. Field of the Invention

The present invention relates generally to orthotic foot appliances, and more particularly to an improved orthotic device for treatment of gait cycle disorders which frequently develop in patients suffering from diabetes, rheumatoid arthritis and certain other conditions.

b. Background

Relevant to the background of the present invention, there will now be a discussion of the following: i) the main components or parts of the human leg and foot; ii) the proper gait cycle which a person goes through in a normal walking motion; and iii) the abnormal gait cycle which develops from diabetes, rheumatoid arthritis or other conditions which impair proper transfer of weight onto the forefoot when walking, and which is corrected by the present invention.

a) The Main Components or Parts of the Human Leg and Foot

With reference to FIGS. 1–3, there is shown a typical human foot 10, and the lower part 12 of the leg 14. The two lower bones of the leg 14 are the tibia 16 and the fibula 18. Below the tibia 16 and fibula 18, there is the talus 20 (i.e., the "ankle bone"). Positioned below and rearwardly of the talus 20 is the calcaneus 22 (i.e., the "heel bone"). Positioned moderately below and forward of the talus 20 are the navicular 24 and the cuboid 26. Extending forwardly from the navicular 24 are the three cuneiform bones 28. Extending forwardly from the cuneiform bones 28 and from the cuboid 26 are the five metatarsals 30. Forwardly of the metatarsals 30 are the phalanges 32 which make up the five toes 34.

The movement of the talus 20 relative to the tibia 16 and fibula 18 is such that it enables the entire foot to be articulated upwardly and downwardly (in the motion of raising or lowering the forward part of the foot). However, the talus 20 is connected to the tibia 16 and fibula 18 in such a way that when the entire leg 14 is rotated about its vertical axis (i.e., the axis extending the length of the leg), the talus 20 rotates with the leg 14.

With regard to the relationship of the talus 20 to the calcaneus 22, these move relative to one another about what is called the "subtalar joint" indicated at 36. The subtalar joint 36 can be described generally as a hinge joint about which the talus 20 and calcaneus 22 articulate relative to one another. The hinge axis extends upwardly and forwardly at an angle of about 42° from the horizontal, and also slants forwardly and inwardly at a moderate angle (e.g., about 16° from a straightforward direction). There is also the midtarsal joint 38, which is in reality composed of two separate joints, the talo-navicular and the calcaneal-cuboid.

b) Gate Cycle of a Normal Foot

During the normal walking motion, the hip (i.e., the pelvis) moves on a transverse plane. Also, the femur (i.e., the leg bone between the knee joint and the hip) and the tibia rotate about an axis parallel to the length of the person's leg. This rotation of the leg about its vertical axis is interdependent with the pronating and supinating of the foot during the gait cycle. There is also flexion and extension of the knee and the ankle joint.

At the beginning of the normal gait cycle the heel of the forwardly positioned leg strikes the ground, after which the forward part of the foot rotates downwardly into ground engagement. The leg then continues through its walking motion to extend rearwardly and the person pushes off from the ball of the foot as the other leg comes into ground engagement.

The phases that make up the gait cycle can be seen in FIG. 4. When the leg is swung forwardly and makes initial ground contact, at the moment of ground contact the leg is rotated moderately to the outside (i.e., the knee of the leg is at a more outward position away from the centerline of the body) so that the foot is more toward the supinated position. However, as the person moves further through the gait cycle toward the 25% position, the leg rotates about its vertical axis in an inside direction so that the subtalar joint is pronating. The effect of this is to rotate the heel of the foot so that the point of pressure or contact moves forwardly from an outside rear heel location (shown at 52 in FIG. 5) towards the location indicated at 54 in FIG. 5. This pronating of the subtalar joint 36 produces a degree of relaxation of the midtarsal joint 38 and subsequent relaxation of the other stabilization mechanisms within the arch of the foot, which reduces the potential shock that would otherwise be imparted to the foot by the forward part of the foot making ground contact.

With further movement from the 25% to the 75% position, the leg rotates in an opposite direction (i.e., to the outside so that the midtarsal joint 38 becomes supinated at the 75% location of FIG. 4. This locks the midtarsal joint 38 so that the person is then able to operate his foot as a rigid lever so as to rise up onto the ball of the foot and push off as the other leg moves into ground contact at a more forward location.

With reference again to FIG. 5, it will be seen that the initial pressure at ground contact is at 52 and moves laterally across the heel to the location at 54. Thereafter, the pressure center moves rather quickly along the broken line indicated at 56 toward the ball of the foot. As the person pushes off from the ball of the foot and then to some extent from the toes of the foot, the center of pressure moves to the location at 58.

c) Abnormal Gait Cycle of the Foot of a Person Suffering From Diabetes or Rheumatoid Arthritis FIG. 6 shows a side view of the foot 60 of a person suffering from diabetes or rheumatoid arthritis, this view being essentially identical to the corresponding view of the normal foot that is shown in FIG. 2.

A common problem is that people suffering from these conditions tend to avoid using their toes when they walk. Typically, this is because of the pain that exists in the areas of the ball of the foot 62 (under the metatarsal heads) and the toes 64. Furthermore, in the case of a diabetic condition, the poor circulation caused by this disease frequently leads to the development of painful sores in those areas which are subjected to repeated pressure or friction, again especially under the ball of the foot and toes.

Because of the discomfort, a person suffering from rheumatoid arthritis or diabetes learns more or less unconsciously to minimize the pressure on the forward portion of the foot when walking, resulting in the abnormal gait cycle that is illustrated in FIG. 7. These views show the person's right foot and lower leg, and correspond to the views shown in FIG. 4. As can be seen, during the initial phases the action of the person's foot is essentially the same as in a normal gait cycle. However, when the person's foot moves from the 50% point towards the 75% point in the cycle, as is shown in the fourth view, the weight begins to be transferred forwardly and generally towards the area of the first metatarsal head, as indicated above with reference to FIG. 5. If rheumatoid arthritis is present in the forefoot area, this causes the person significant pain or discomfort, which tends to increase in intensity as the weight moves forwardly towards the toes. Consequently, the person seeks to reduce the pain by avoiding transfer of weight forwardly beyond the ball of the foot, with the result that the normal "toe-off" action does not occur; instead, the foot is lifted away from the ground more or less horizontally at the end of the gait cycle, as is shown in the right-hand view of FIG. 7.

Over time, this action becomes automatic, so that the person develops a shuffling gait in which the feet simply flatten out after heel strike and then lift off again in a horizontal orientation. This abnormal gait cycle is extremely inefficient, and frequently leads to development of other problems in the person's feet and legs. Moreover, the constant pressure on the ball of the foot at the end of the abortive gait cycle tends to "squeeze" the blood out of the comparatively thin layer of tissue that exists under the bones in this part of the foot, eventually leading to development of sores and serious tissue damage.

Although the shuffling gait cycle and lack of toe-off described above are commonly associated with rheumatoid arthritis and diabetes, it will be understood that there are other conditions affecting the leg and/or foot that can lead to similar problems. For example, a condition of functional hallux limitus (often resulting from arthritis in or at the base of the large toe, from an elevated first ray, or from some other structural malformity) can precipitate foot and gait problems very much like those described above.

There have been previous attempts to treat these problems by devising a special shoe having a rocker bottom, in an effort to move the person's foot into more of a toe-off position before the end of the gait cycle. However, this solution is excessively expensive and the special shoes are uncomfortable and difficult to use, especially for elderly patients. However, if the condition is left untreated additional foot and leg problems can develop, and in some cases the damage to the foot may progress to the point where a partial or full amputation is required.

Accordingly, there exists a need for a device which facilitates proper toe-off by the foot at the end of the gait cycle, so as to ensure proper foot motion and avoid development of an improper shuffling gait, particularly in individuals suffering from rheumatoid arthritis, diabetes, functional hallux limitus or other conditions that prevent the normal transfer of weight onto the forefoot portion of the foot. Furthermore, there exists a need for such a device that induces proper toe-off at the end of the gait cycle without causing pain in toes and forefoot portions of a foot of a person suffering from rheumatoid arthritis, diabetes or similar condition. Still further, there exists a need for such a device that can be used with a conventional shoe, both for convenience and to minimize the cost to the user, and also to permit the user to employ a single device or pair of devices with several different shoes. Still further, there exists a need for such a device that can be shaped to meet the contours and specific requirements of the feet of individual users. Still further, there exists a need for such a device that can be manufactured in a quick, efficient and economical manner, and that is durable and long lasting and will sustain extended use without collapsing, breaking, or otherwise undergoing significant deterioration.

SUMMARY OF THE INVENTION

The present invention has solved the problems cited above, and is an orthotic insert that is removably insertable in a shoe for providing enhanced orientation of a foot at the toe-off position of the gait cycle.

Broadly, the insert comprises a substantially rigid cap member for engaging a plantar surface of a person's foot, the cap member having a rearward portion for extending beneath an arch and rearfoot portion of a person's foot, a forward portion for extending to a position at least proximal the metatarsal head portion of the foot, and a ridge portion extending downwardly from the cap member proximate the junction between the forward and rearward portions thereof for engaging an upper surface of an insole of the shoe so as to form a pivot point that causes the cap member to tilt forwardly in response to a shift in weight from the rearfoot portion to the forefoot portion of the foot, so that as weight shifts forwardly on the foot as the orthotic insert tilts forwardly in the shoe so as to orientate the foot at increased forward angle at the toe-off position of the gait cycle.

A ridge portion may extend transversally across the bottom of the rigid cap member, and may be formed integrally with the cap member. The ridge portion may extend at an angle that is substantially parallel to an angle of a row of metatarsal heads of the foot. The transverse ridge portion may be positioned proximate to and slightly rearwardly of the metatarsal head area of the foot, so that the cap member tilts forwardly in response to weight being transferred forwardly towards the metatarsal head area.

The rearward portion of the rigid cap member may include a curved arch portion following an arch portion of the foot, while the forward portion of the cap member may include a metatarsal flange portion for extending forwardly beneath the metatarsal head area of the foot along the transverse plane of the foot. The ridge portion may be formed substantially level with the flange portion of the cap member, at a location a spaced distance rearwardly from a position of the metatarsal head area of the foot, so that at this location the ridge portion extends a predetermined vertical height below the arch portion of the cap member.

The rigid cap member of the insert may have a forward edge for being positioned proximate the metatarsal head area of the foot. The forward edge of the cap member may extend at an angle substantially parallel to the angle of the row of metatarsal heads of the foot. The insert may further comprise a forefoot extension mounted to the flange portion and extending forwardly therefrom for transmitting downward forces from the forefoot portion of the foot to the flange portion of the cap member. The forefoot extension may comprise a layer of resiliently cushioning material mounted to the flange portion of the cap member.

The rigid cap member may be formed of at least one layer of fiber-resin material. The insert may further comprise a resilient, cushioning blank member mounted atop the rigid cap member for engaging a plantar surface of the foot.

These and other features and advantages of the present invention will be apparent from a reading of the following detailed description with reference to the accompanying drawings.

DETAILED DESCRIPTION a. Overview

Figure 8:
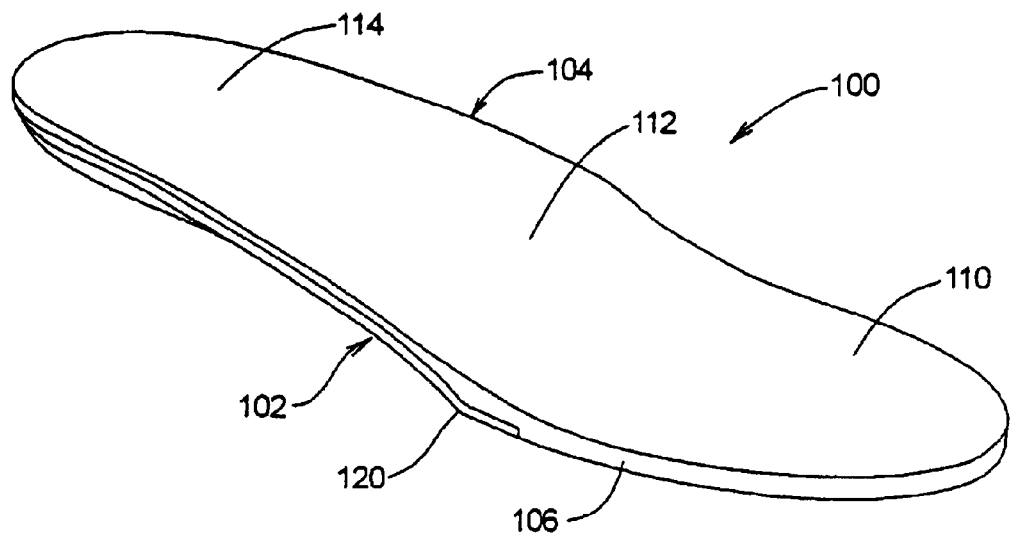
FIG. 8 is a perspective view of an orthotic device in accordance with the present invention, for treatment of the abnormal gait cycle that is shown in FIG. 7, this having a transverse, downwardly extending rocker portion for engaging the upper surface of an insole of shoe so as to create a forward-rocking motion of the foot within the shoe so as to induce proper toe-off motion at the end of the gait cycle.

FIG. 8 shows an orthotic insert 100 in accordance with the present invention, this being sized and configured for removable and interchangeable installation in a wide variety of conventional shoes so as to cooperate with the insoles and other components thereof.

The principal structural member of the insert 100 is a thin, comparatively rigid cap member 102. For the reasons described below, the cap member is preferably formed of molded fiber-resin material, however, the cap member may be formed from any number of suitable materials, such as polyethylene, polypropylene, epoxy, injection molded plastic, metal, fiberglass and graphite-fiber composite materials, for example. Also, although it is comparatively rigid, the cap 102 is preferably formed so as to be resilient and moderately deflectable for comfort and durability in use. A particular feature of the cap member is a downwardly extending ridge which is formed on the lower surface thereof, as will be described in greater detail below.

The cap member 102 is overlain by a soft, flexible, cushioning blank member 104. Because the feet of people suffering from diabetes and rheumatoid arthritis are usually tender and easily damaged, the cushioning blank 104 may be somewhat thicker and softer than would ordinarily be used with a conventional orthotic device, although preferably not so thick as to interfere with the device fitting and functioning comfortably within a conventional shoe. The cushioning blank member may be formed of any suitable material such as foam rubber, FREELIN™, PLASTIZOTE™, PORON™ (which is very soft and comfortable for use with a diabetic foot), or open or closed cell foam, which is characterized as being relatively resilient and having sufficient memory to return to its original state after being stressed. Furthermore, the blank is preferably provided with an abrasion-resistant top cover (not shown) that may be formed of any suitable fabric, such as nylon, felt, cloth, or the like.

As can also be seen in FIG. 8, the blank 104 includes a forefoot extension 106 that is mounted to the forward end of the cap member and extends forwardly therefrom so as to be positioned beneath the ball and toes of the foot. As will also be described in greater detail below, the forefoot extension transmits downward forces from the forefoot to the forward portion of the cap member, especially in those embodiments where a ¾-length (as opposed to full length) cap member is employed. In addition, the forefoot extension provides an area of increased cushioning under the forefoot, and also enables the device to be configured for selective relief of specific pressure points in this area.

Taken as a whole, therefore, the device 100 can be considered as including a forefoot portion 110, an arch portion 112 and a heel portion 114. The rocker portion 120, in turn, extends transversely across the bottom of the cap member 102, approximately at the junction between the arch portion 112 and the forefoot portion 110. As can also been seen in FIG. 9, the rocker portion preferably extends across the entire width of the device and is positioned proximate to or slightly rearwardly of the metatarsal head area of the foot, as indicated at 122. The rocker portion projects downwardly to the forefoot plane at a location somewhat rearwardly of the metatarsal head area of the foot, so that this cooperates with the insole of the shoe to form a pivot point that causes the device to rock forwardly as weight is transferred forwardly on the person's foot, thereby tilting the foot forwardly to an enhanced orientation for toe-off.

b. Cap Member and Rocker Portion

Figure 9:
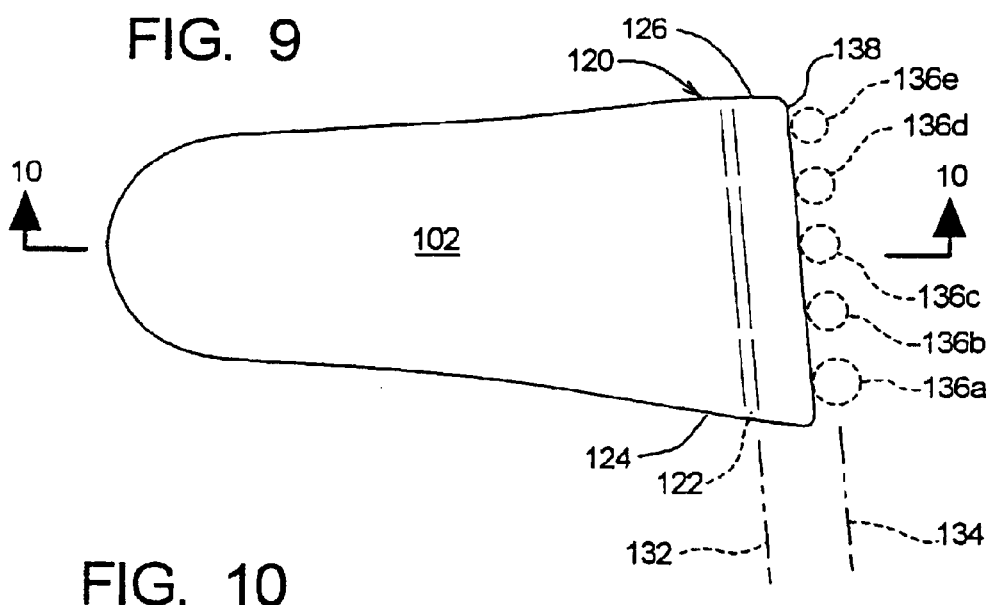
FIG. 9 is a bottom plan view of the orthotic device of FIG. 10, showing the configuration of the rocker portion in greater detail and its location relative to the metatarsal head area of the wearer's foot.
Figure 10:
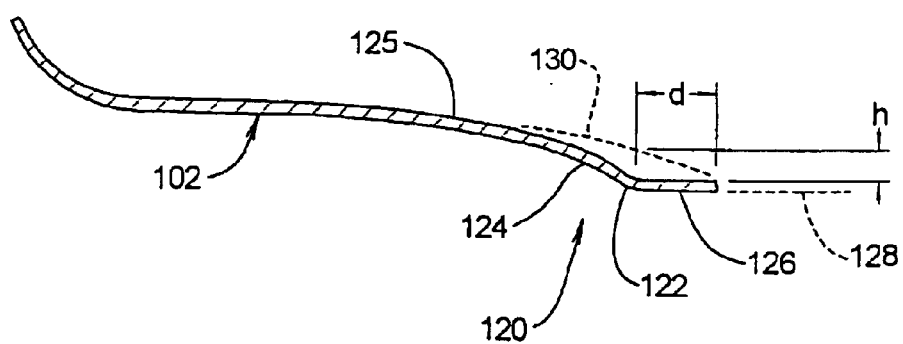
FIG. 10 is a side view of a longitudinal cross-section of the orthotic device of FIGS. 8 and 9, taken along line 10—10, showing the relation of the downwardly protruding rocker portion to the midfoot and forefoot positions of the device in greater detail.

The rigid cap member is the primary structural component of the orthotic insert of the present invention. As can be seen in FIGS. 9–10 the cap member 102 is a thin, rigid, but preferably resiliently flexible member, suitably formed of a fiber-resin material or any of the other materials noted above. The "thinness" of the material (e.g., 1.5–3 mm) is important for minimizing the height occupied in the shoe, while the rigidity is important to the operation of the device, particularly in the area of the rocker section 120. The cushioning blank member is included primarily for user comfort and is somewhat optional, i.e. it may not be present in other embodiments.

As is shown in FIG. 10, the rocker portion 120 includes a transverse ridge 122 that is formed at the junction between a down-curved forward edge 124 of the arch portion 125 of the cap, and a comparatively short metatarsal flange portion 126. The flange portion extends forwardly generally within the transverse plane of the foot, as indicated by dotted line 128, while the front edge of the arch portion bends downwardly below the curved path of the arch, as indicated by dotted line 130. Consequently, the ridge 122 is located a spaced distance "d" rearwardly of the metatarsal head area of the foot, so as to be positioned a spaced height "h" below the arch at this point. Because the insole of the shoe will also be downcurving at this location (to accommodate the arch of the foot), the ridge will support the forefoot portion of the insert at a spaced height above the forefoot portion of the insole, when the heel portion of the cap member is in contact with the heel portion of the insole, thereby forming a pivot point between the forefoot and rearfoot portions of the device.

The height of the ridge is selected according to the amount of "rocking" action that is desired and the condition and circumstances of the individual foot, and also according to the type of shoe with which the device is to be used. For example, suitable heights "h" for the ridge 122 range from about 1/16 inch to about 1/4 inch or more, with 3/16 inch being optimal for many applications. The spacing, and therefore the range of tilting motion, may also be increased by angling the forward end of the cap member and/or the forefoot extension upwardly away from the forward end of the insole.

Moreover, while in the preferred embodiment illustrated herein the ridge portion is formed in the manner of a fold or crease in the cap member, in other embodiments the ridge may have more of a raised contour, for example, to increase the range of motion, and also may be more rounded on its lower surface so as to impart more of a smooth, rolling action to the motion of the device.

As can be seen with further reference to FIG. 9, the ridge 122 extends across the cap member along an axis 132 that angles somewhat rearwardly from the medial side of the lateral side of the foot, so as to extend generally parallel to a transverse axis 134 that is defined by the row of metatarsal heads 136a–e. Consequently, as the weight is transmitted from the foot to the cap member and the device begins to pivot forwardly, the pressure is shared more or less equally among the metatarsal heads, thus ensuring an even pivoting motion and also avoiding undesirably concentration of pressure against the foot; it will be understood, however, that in some embodiments one side of the foot or the other may be found to be comparatively stronger or more painful, and it may be advantageous to adjust the angle of the ridge accordingly.

In the embodiment that is illustrated, the forward edge 138 of the metatarsal flange 126 of the cap member lies just proximal the location of the metatarsal heads 136a–e of the foot. This embodiment, therefore, relies primarily on the forefoot extension 106 to transmit downward loads from the metatarsal heads/forefoot to the cap member. It will be understood, however, that in some embodiments the flange portion of the rigid cap member may continue forwardly beneath the metatarsal heads and forefoot (and consequently obviate the need for a forefoot extension), or in other embodiments it may terminate somewhat rearwardly of the location that is shown in FIG. 9.

c. Operation

Figure 11A:
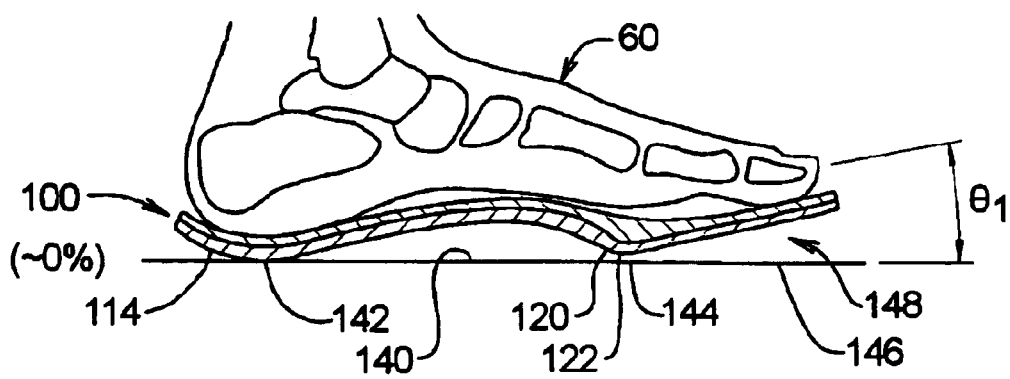
FIGS. 11A—11C are sequential views, somewhat schematic in nature, showing the manner in which the rocker portion of the orthotic device of the present invention cooperates with the insole of the wearer's shoe to create a rocking motion in response to the forward weight transfer of a person's foot, which improves the orientation of the foot and induces a proper toe-off motion at the end of the cycle.
Figure 11B:
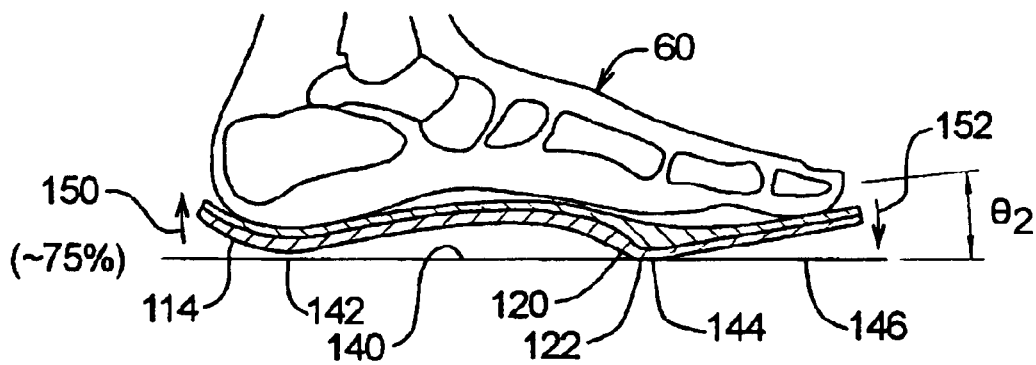
Figure 11C:
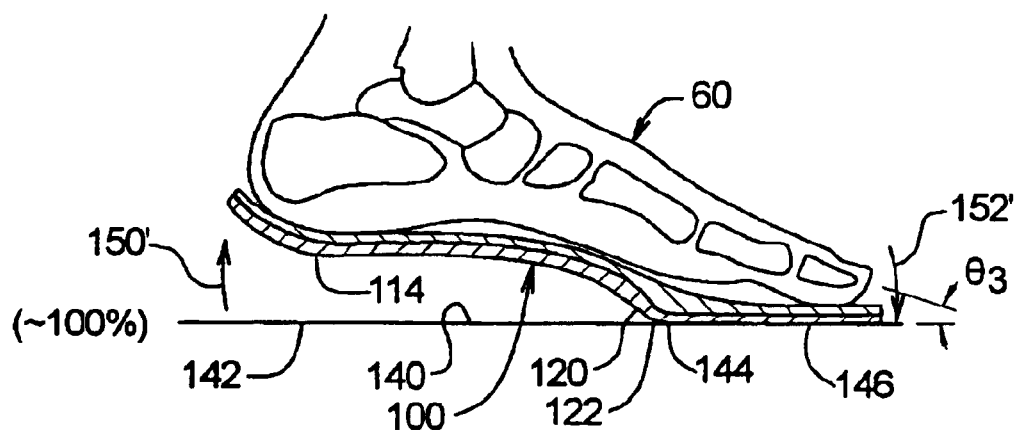

FIGS. 11A–C illustrate the manner in which the orthotic device 100 creates a tilting or "rocking" motion that encourages proper toe-off and propulsion at the end of the gait cycle. For purposes of illustration, the drawings show a somewhat exaggerated range of motion. Also for the sake of clarity the insole of the shoe has been shown as a straight line, however, it should be understood that in most cases the insole would have a somewhat curved contour, particularly in the arch area as noted above.

Accordingly, FIG. 11A shows the foot in the heel strike position. In this position the person's weight is concentrated toward the heel, in the area corresponding to pressure points 52–54 in FIG. 5, with the result that the rigid cap member 102 cooperates with the insole 140 of the shoe so that the heel portion 114 of the device is forced downwardly into contact with the heel area 142 of the insole. At the same time, because the interaction between ridge 122 and the insole 140 provides a forwardly located pivot point 144, the forward end 110 of the device tilts upwardly away from the forefoot area 146 of the insole, forming a gap 148 between the two. As a result, the forefoot portion of the device and the transverse plane of the foot assume an elevated angle $\theta_1$ relative to the insole, which accommodates the forward tilting action of the orthotic during the subsequent phases of the cycle.

Figure 1:
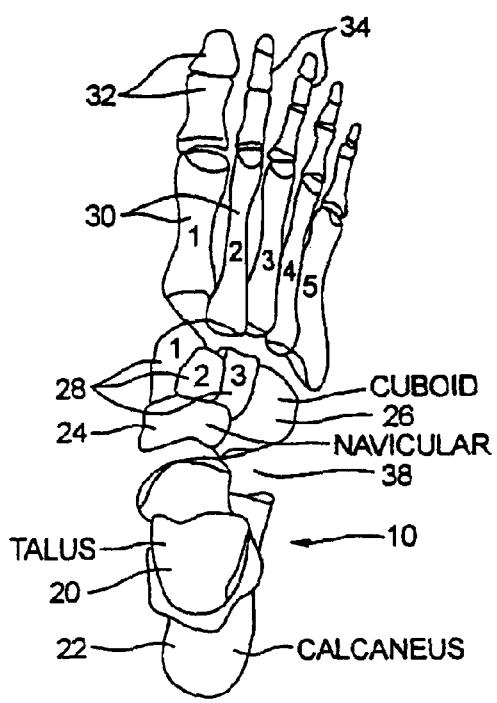
FIG. 1 is a top plan view of the right foot of a human with certain components of the foot being separated from one another for purposes of illustration.
Figure 2:
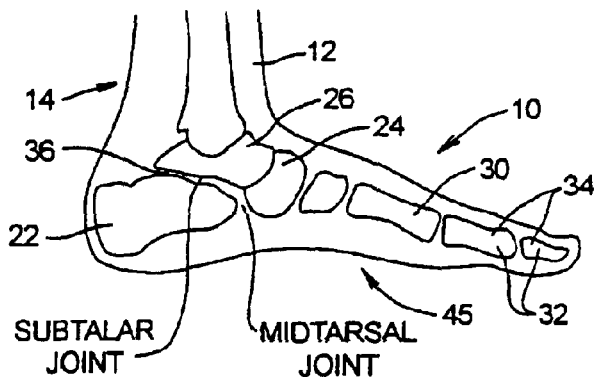
FIG. 2 is a side elevational view looking toward the inside of a person's left foot, with the outline of the foot and lower leg being shown as a shaded area.
Figure 3:
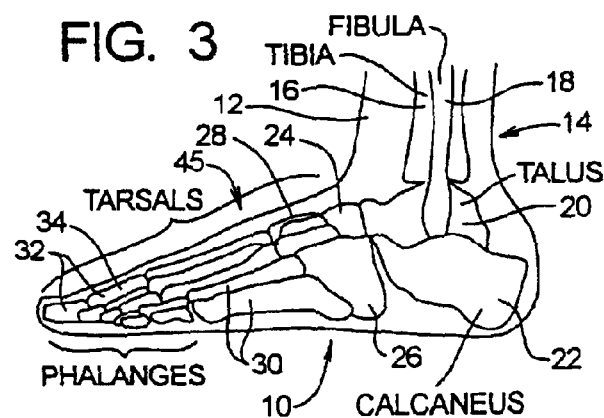
FIG. 3 is a view similar to FIG. 2, but looking toward the outside of the person's foot.
Figure 4:
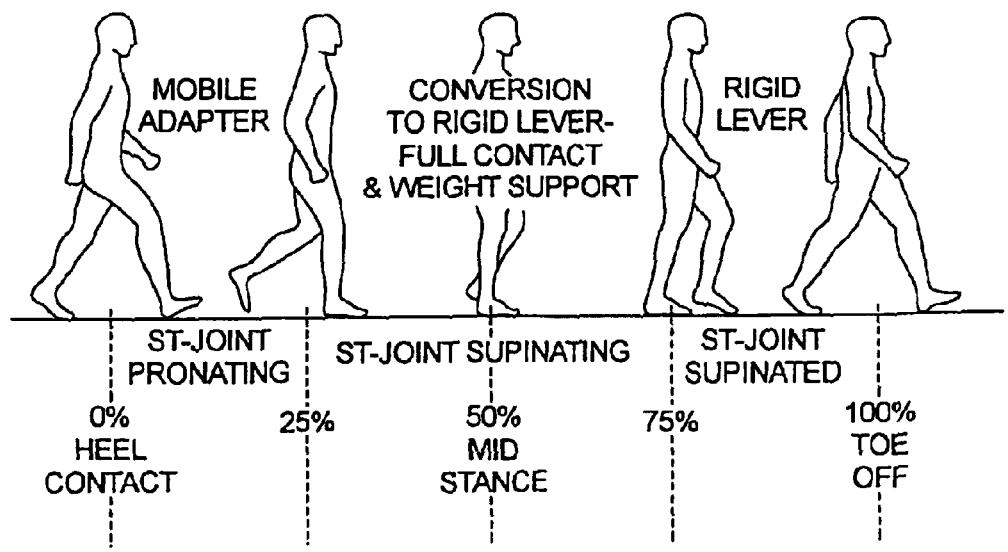
FIG. 4 is a sequential, graphical view, illustrating the timing of the pronating and supinating motion of the leg and foot through the gait cycle.
Figure 5:
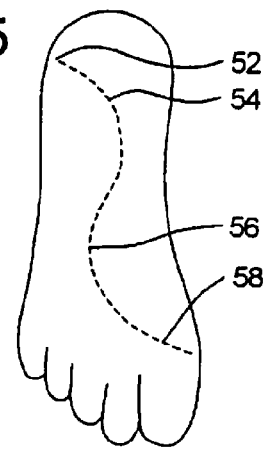
FIG. 5 is a view looking upwardly toward the plantar surface of a person's left foot, illustrating the distribution or location of the center of pressure throughout the period of ground contact during the gait cycle illustrated in FIG. 4.
Figure 6:
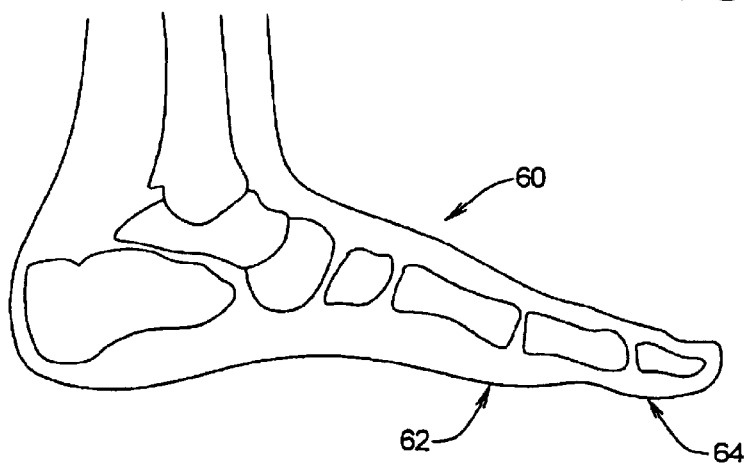
FIG. 6 is a side elevational view of a person's foot, similar to FIG. 2 above, showing those particular areas of the foot in which pain tends to develop due to diabetes or rheumatoid arthritis.
Figure 7:
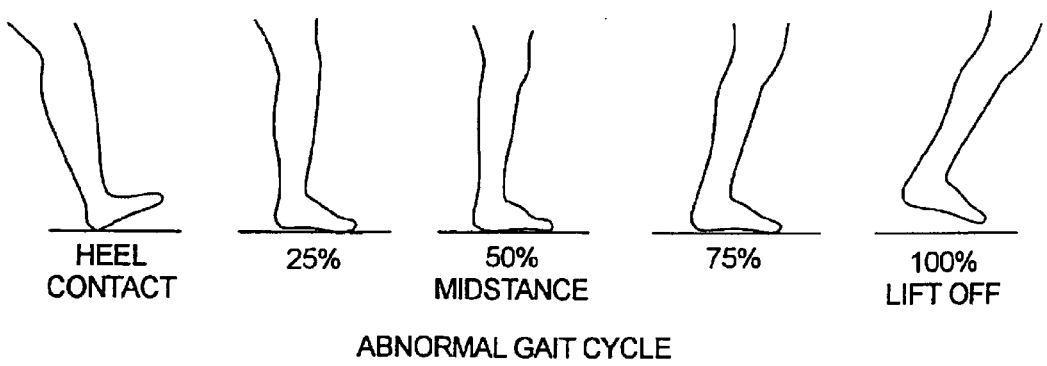
FIG. 7 is a sequential view, similar to FIG. 4, illustrating the ground contact phases of the abnormal, shuffling gait cycle that typically develops as a result of the forefoot pain caused by diabetes or rheumatoid arthritis.

During the next phase of the gait cycle, as can be seen in FIG. 11B, the person's weight begins to be transferred forwardly, towards the area corresponding to pressure point 56 in FIG. 5. As this occurs, the concentration of weight begins to shift forwardly of the rocker portion 120, so that the heel end of the device begins to lift in the direction indicated by arrow 150 and at the same time the forward end of the device begins to pivot downwardly in the direction indicated by arrow 152. As a result, the forefoot portion of the foot 60 pivots to a reduced angle $\theta_2$ relative to the transverse plane of the insole.

With continued forward shifting of weight (see pressure point 58 in FIG. 5), the forefoot portion of the device continues to pivot downwardly around rocker portion 120, in the direction indicated by arrow 142 in FIG. 11C, while at the same time (due to the rigidity of the cap member) the heel portion rises and lifts the back of the foot, in the direction indicated by arrow 150'. Thus, as the foot reaches the end of the gait cycle, the metatarsal flange and forefoot plane of the device are tipped forwardly to an angle $\theta_3$ which may be actually depressed relative to the forefoot area 146 of the insole, so that the foot 60 is moved to an artificially enhanced "toe-off" orientation which approximates the correct orientation for the toe-off phase of a normal gait cycle. This overcomes the "shuffling" orientation that the person has developed due to diabetes, rheumatoid arthritis, or other condition, and provides for proper propulsion and operation of the foot and leg during the final phases of the gait cycle.

Following toe-off, the foot 60 and orthotic device 100 tilt back rearwardly within the shoe, and return to the orientation shown in FIG. 11A in preparation for the next heel strike.

d. Molding and Fabrication

Figure 12:
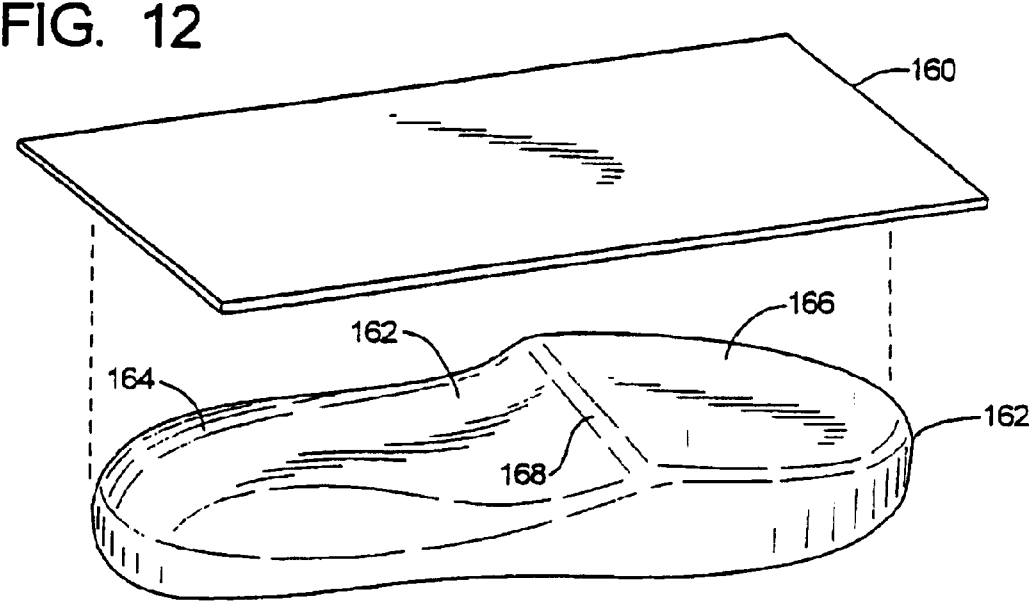
FIG. 12 is a perspective view of a male mold taken from a patient's foot and moldable fiber-resin sheet material that is formed over the cast to produce the rigid cap member of the orthotic device of FIGS. 8–10, with a raised ridge being built up on the surface of the mold for forming the rocker portion of the device.
Figure 13:
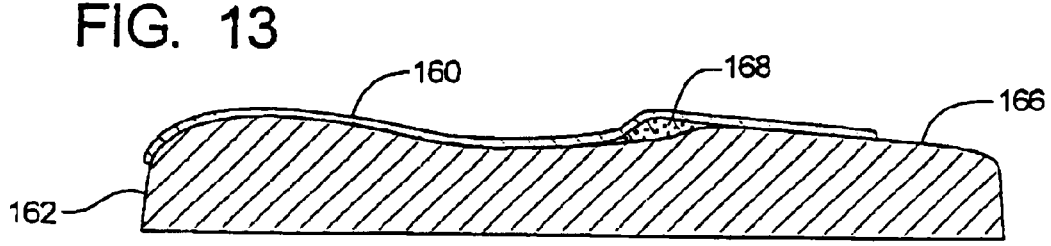
FIG. 13 is a cross-sectional view, taken longitudinally through the mold and layer of fiber-resin material of FIG. 12 as these are brought together to shape the cap member, showing the height of the raised ridge on the mold which forms the rocker portion of the device.
Figure 14:
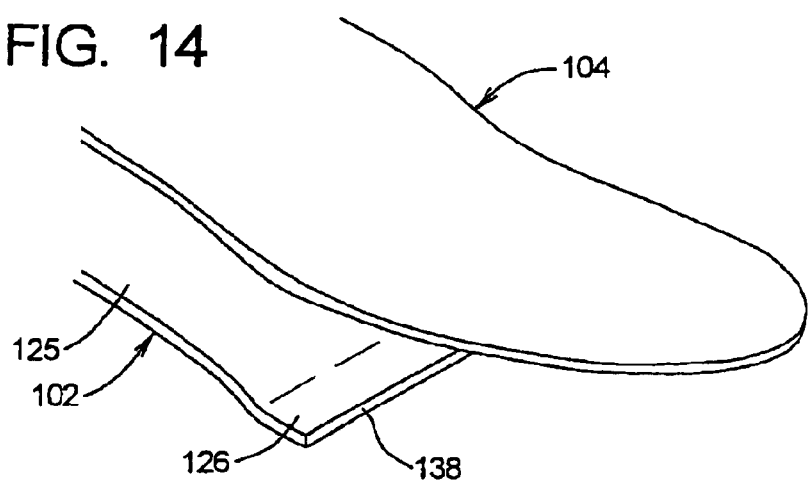
FIG. 14 is a partial, exploded view of the forefoot end of the orthotic device of FIGS. 8–10, showing the layer of cushioning material which is mounted atop the forefoot end of the rigid cap to provide increased comfort beneath the ball of the foot and toes at toe-off.

FIGS. 12–14 illustrate the manufacture of an orthotic device as described above, in accordance with a preferred embodiment of the present invention.

In the illustrated embodiment, the cap member is formed of a molded fiberglass-resin material in which the uncured resin matrix is soft and readily moldable, and becomes hard and rigid (but still resiliently flexible) when heated and cured. Such materials are commonly being referred to as "pre-preg" and are available in sheet form from Hexcel Corporation, Dublin, Calif., and many other suppliers. The fiberglass resin material may be used alone, or in combination with layers of other material, such as graphite fiber-resin material, to provide particular strength or control characteristics.

FIG. 12 thus shows a planar layup unit 160 which may be formed of a single layer of the uncured fiberglass-resin material, or may a laminated unit made up of two or more layers of uncured material. The layup unit 160 is dimensioned to have an area slightly larger than that of the final cap member, so as to allow for trimming and removal of material during finishing.

As can be seen with further reference to FIG. 12, the uncured layup unit is placed in contact with the surface of a positive mold 162, with the contour of the mold corresponding to that of the plantar surface of a human foot. The positive mold may be taken from a plaster cast of a patient's foot, so as to form a custom-made device, or may be based on a conventionalized or "standard" foot for more of a universal fit. The contours from the arch area 164 rearwardly through the heel area 168 correspond directly to the shape of the foot, however, the forward portion 166 of the mold surface is generally planar and corresponds to the transverse plane of the finished cap member. A raised ridge 170 is formed at the juncture between the arch area 164 and planar forward area 168, so as to shape the ridge portion in the finished article. As can be seen in FIG. 13, the ridge 170 is suitably formed by building up the surface of the mold in the area behind the metatarsal heads of the foot, using a layer or strip of plaster or other material of the appropriate thickness.

The ridge 170 is contoured to provide a smooth transition where this tapers off into the forefoot and arch areas, however, it will be understood that somewhat different contours may be employed in some embodiments, so long as the desired raised ridge is formed in the finished article. Also, it will be understood that in some embodiments, rather than being formed of plaster or the like as in the illustrated embodiment, the mold may be constructed by other means, such as by a machined or multi-element mold surface, and the ridge portion may be included in the initial formation of the mold, rather than by subsequently building up material as shown.

As can be seen with further reference to FIG. 13, the layup unit 160 is forced against the surface of the mold 162 so that the soft, deformable material of the uncured layup unit conforms to and assumes the contours of the mold, including the ridge portion 170. The layup unit may be pressed against the surface by any suitable means, such as by a diaphragm or by hand, for example.

The mold 162 and layup unit 160 are then placed in an oven, at a temperature and for a time sufficient to effect curing of the resin matrix, as specified by the manufacturer of the fiber-resin material. Upon cooling, the now rigid layup unit is removed and trimmed to form the finished cap member 102, with the forward edge 138 being cut off along the line of the metatarsal heads of the foot as described above.

As is shown in FIG. 14, the cushioning blank member 104 is mounted atop the finished cap member 102, using adhesive or other suitable means, so that the blank member assumes the contour of the cap member and therefore that of the plantar surface of the person's foot. However, as was noted above, the cushioning blank member may not be present in all embodiments. For example, in some embodiments the metatarsal flange may extend forwardly beneath the forefoot area, to receive the downward pressure of the separate forefoot in place of the forefoot extension; in general, however, in those embodiments having a ¾ length cap member as shown (i.e., where the cap member terminates at or rearwardly of the metatarsal heads), some form of forefoot extension, whether formed by the cushioned blank or otherwise, will generally be present in order to receive and transfer the downward weight of the forefoot so as to effectuate the tilting/rocking motion of the assembly.

Conversely, the cushioned blank may be configured to provide additional functions complementary to that of the tilt/rocking motion provided by the cap member; for example, the forefoot extension portion 110 of the cushioned blank member may be provided with recesses or cutouts for accommodating tender or sore areas or malformations of a foot, or may be provided with one or more thickened, raised areas for providing additional support in desired areas under the toes.

It is to be recognized that these and various other alterations, modifications, and/or additions may be introduced into the constructions and arrangements of parts described above without departing from the spirit or ambit of the present invention as defined by the appended claims.

What is claimed is:

1. An orthotic insert that is removably insertable in a shoe for providing enhanced orientation of a foot at a toe-off position of a gait cycle, said orthotic insert comprising:

a substantially rigid cap member for engaging a plantar surface of a person's foot, said rigid cap member having a rearward portion for extending beneath an arch and rear foot portion of a person's foot, and a forward portion for extending to a position at least proximal a metatarsal head portion of said foot;

a ridge portion extending downwardly from said rigid cap member proximate a junction between said forward and rearward portions thereof for engaging an upper surface of an insole of said shoe so as to form a pivot point, said ridge portion being located a spaced distance rearwardly of said metatarsal head portion and extending downwardly beneath said arch portion by a distance sufficient that said forward portion of said cap member is supported a spaced distance above a forefoot portion of said insole when said rearward portion of said cap member is in contact with a heel portion of said insole;

so that in response to weight shifting forwardly from said rearward portion of said cap member to said forward portion as said foot progresses through said gait cycle, said forward portion of said cap member pivots downwardly towards said forefoot portion of said insole and said rearward portion pivots upwardly from said rearfoot portion of said insole so that said orthotic insert tilts forwardly in said shoe so as to orientate said foot at an increased forward angle at said toe-off position.

2. The orthotic insert of claim 1, wherein said ridge portion extends transversely across a bottom of said rigid cap member.

3. The orthotic insert of claim 2, wherein said ridge portion is formed integrally with said rigid cap member.

4. The orthotic insert of claim 2, wherein said transverse ridge portion is positioned proximate to and slightly rearwardly of a metatarsal head area of said person's foot, so that said rigid cap member tilts forwardly in response to transfer of weight toward said metatarsal head area.

5. The orthotic insert of claim 4, wherein said rearward portion of said rigid cap member includes a curved arch portion for following an arch of portion of said foot, and said forward portion of said cap member includes a metatarsal flange portion for extending forwardly under said metatarsal head area along a transverse plane of said foot.

6. The orthotic insert of claim 5, wherein said ridge portion is substantially level with said flange portion of said cap member and is formed at a location a spaced distance rearwardly from a position of said metatarsal head area of said foot, so that at said location said ridge portion extends a predetermined vertical height below said arch portion of said cap member.

7. The orthotic insert of claim 6, wherein said flange portion of said rigid cap member has a forward edge for being positioned proximate said metatarsal head area of said foot.

8. The orthotic insert of claim 7, wherein said insert further comprises:
a forefoot extension mounted to said flange portion and extending forwardly therefrom for transmitting downward forces from said forefoot portion of said foot to said flange portion of said rigid cap member.

9. The orthotic insert of claim 8, wherein said forefoot extension comprises:
a layer of resiliently cushioning material mounted to said flange portion of said cap member.

10. The orthotic insert of claim 1, further comprising:
a resilient, cushioning blank member mounted atop said rigid cap member for engaging a plantar surface of said foot.

11. The orthotic insert of claim 1, wherein said rigid cap member is formed of at least one layer of fiber-resin material.

12. The orthotic insert of claim 1, wherein said ridge portion extends across said rigid cap member at an angle substantially parallel to an angle defined by a row of metatarsal heads of said foot.

13. The orthotic insert of claim 12, wherein said rigid cap member has a forward edge that extends at an angle substantially parallel to said ridge portion and said row of metatarsal heads of said foot.

14. A removable orthotic insert for providing enhanced orientation of a foot at a toe-off position of a gait cycle, said orthotic insert comprising:
a thin, substantially rigid cap member having an upper surface for engaging a plantar surface of said foot and a lower surface for engaging an insole of a shoe, said rigid cap member comprising:
a generally concave rearfoot portion for engaging a heel portion of said foot;
a generally downcurved midfoot portion for engaging an arch portion of said foot;
a generally planar forefoot portion for engaging a metatarsal head portion of said foot; and
a ridge portion formed at a junction between said forefoot portion and said midfoot portion for engaging said insole so as to provide a pivot point for said cap member;
said ridge portion of said cap member being located a spaced distance rearwardly of said metatarsal head portion and extending downwardly beneath said arch portion by a distance sufficient that said forefoot portion of said cap member is supported a spaced distance above a forefoot portion of said insole when said rearfoot portion of said cap member is in contact with a heel portion of said insole;
so that in response to transfer of weight forwardly from said heel portion towards said metatarsal head portion of said foot as said foot progresses through said gait cycle, said forefoot portion of said cap member pivots downwardly towards said forefoot portion of said insole and said rearfoot portion of said cap member pivots upwardly from said heel portion of said insole so as to tilt said foot forwardly to said enhanced orientation at said toe-off position.

15. The orthotic insert of claim 14, wherein said ridge portion extends transversely across said cap member at an angle generally parallel to an angle defined by a row of metatarsal heads of said foot.

16. The orthotic insert of claim 15, wherein said forefoot portion of said rigid cap member comprises a short, generally planar metatarsal flange portion having a forward edge for terminating proximate said metatarsal head area of said foot.

17. The orthotic insert of claim 16, wherein said forward edge of said flange portion extends across said rigid cap member at an angle substantially parallel to said angle of said ridge portion of said cap member.

18. The orthotic insert of claim 17, wherein said insert further comprises:
a forefoot extension mounted to said flange portion and extending forwardly therefrom for transmitting downward forces to said flange portion as weight is transferred forwardly on said foot.

19. The orthotic insert of claim 18, wherein said forefoot extension comprises:
a layer of resilient cushioning material mounted to an upper surface of said flange portion.

20. The orthotic insert of claim 19, wherein said layer of resilient cushioning material extends over substantially the full length of said rigid cap member for engaging and cushioning said plantar surface of said foot.

21. An apparatus for providing enhanced orientation of a foot at a toe-off position of a gait cycle, said apparatus comprising in combination:
a shoe having an insole, and
an orthotic insert removably inserted in said shoe for engaging a person's foot, therein, said orthotic insert comprising:
a substantially rigid cap member for engaging a plantar surface of a person's foot, said rigid cap member having a rearward portion for extending beneath an arch and rear foot portion of a person's foot, and a forward portion for extending to a position at least proximal a metatarsal head portion of said foot; and
a ridge portion extending downwardly from said rigid cap member proximate a junction between said forward and rearward portions thereof for engaging an upper surface of an insole of said shoe so as to form a pivot point, said ridge portion being located a spaced distance rearwardly of said metatarsal head portion and extending downwardly beneath said arch portion by a distance sufficient that said forward portion of said cap member is supported a spaced distance above a forefoot portion of said insole when said rearward portion of said cap member is in contact with a heel portion of said insole;
so that in response to weight shifting forwardly from said rearward portion of said cap member onto said forward portion as said foot progresses through said gait cycle, said forward portion of said cap member pivots downwardly towards said forefoot portion of said insole and said rearward portion pivots upwardly from a rearfoot portion of said insole so that said orthotic insert tilts forwardly in said shoe so as to orientate said foot at an increased forward angle at said toe-off position.

* * * * *